(12) United States Patent
Scheller (10) Patent No.: US 7,872,041 B2
(45) Date of Patent: Jan. 18, 2011

(54) USE OF ROTIGOTINE FOR TREATING AND PREVENTING PARKINSON'S PLUS SYNDROME

(75) Inventor: Dieter Scheller, Neuss (DE)

(73) Assignee: UCB Pharma GmbH, Monheim (DE)

( * ) Notice: Subject to any disclaimer, the term of this patent is extended or adjusted under 35 U.S.C. 154(b) by 802 days.

(21) Appl. No.: 10/593,964

(22) PCT Filed: Mar. 22, 2005

(86) PCT No.: PCT/EP2005/003013
§ 371 (c)(1), (2), (4) Date: Sep. 22, 2006

(87) PCT Pub. No.: WO2005/092331
PCT Pub. Date: Oct. 6, 2005

(65) Prior Publication Data
US 2007/0191470 A1    Aug. 16, 2007

(30) Foreign Application Priority Data
Mar. 24, 2004 (DE) .................. 10 2004 014 841

(51) Int. Cl.
*A61K 31/381* (2006.01)
*A61P 25/14* (2006.01)
(52) U.S. Cl. ..................... 514/438; 514/447
(58) Field of Classification Search ............... 514/438, 514/447
See application file for complete search history.

(56) References Cited

U.S. PATENT DOCUMENTS

| | | | |
|---|---|---|---|
| 4,542,135 A | 9/1985 | Kobel et al. ............. 514/250 |
| 4,564,628 A | 1/1986 | Horn .................... 514/438 |
| 4,722,933 A | 2/1988 | Horn .................... 514/438 |
| 4,824,860 A | 4/1989 | Owen ................... 514/418 |
| 4,847,253 A | 7/1989 | Buonamici et al. ......... 514/253 |
| 4,885,308 A | 12/1989 | Horn .................... 514/438 |
| 5,071,875 A | 12/1991 | Horn .................... 514/613 |
| 5,151,446 A | 9/1992 | Horn et al. .............. 514/617 |
| 5,177,112 A | 1/1993 | Horn .................... 514/65 |
| 5,234,945 A | 8/1993 | Belluzzi |
| 5,382,596 A | 1/1995 | Sleevi et al. ............. 514/459 |
| 5,456,745 A | 10/1995 | Roreger et al. ........... 106/128 |
| 5,486,611 A | 1/1996 | Lin et al. ............... 546/62 |
| 5,496,843 A | 3/1996 | Nagata et al. ............ 514/411 |
| 5,545,755 A | 8/1996 | Lin et al. ............... 564/428 |
| 5,614,518 A | 3/1997 | Leeson et al. ............ 514/234.5 |
| 5,633,376 A | 5/1997 | Thurkauf et al. .......... 544/360 |
| 5,681,956 A | 10/1997 | Thurkauf et al. .......... 544/295 |
| 5,807,570 A | 9/1998 | Chen et al. .............. 424/449 |
| 5,807,855 A | 9/1998 | Bogeso et al. ............ 514/449 |
| 5,891,461 A | 4/1999 | Jona et al. .............. 424/449 |
| 6,001,861 A | 12/1999 | Oertel et al. ............ 514/367 |
| 6,010,877 A | 1/2000 | Sathe et al. ............. 435/69.1 |
| 6,107,318 A | 8/2000 | Pocchiari et al. ......... 514/367 |
| 6,221,627 B1 | 4/2001 | Sathe et al. ............. 435/69.1 |
| 6,227,875 B1 | 5/2001 | Wu et al. ................ 514/367 |
| 6,331,636 B1 | 12/2001 | Romero et al. ........... 548/235 |
| 6,372,920 B1 | 8/2002 | Minaskanian et al. ...... 549/75 |
| 6,884,434 B1 | 4/2005 | Muller et al. ............ 424/487 |
| 7,309,497 B2 | 12/2007 | Rimpler et al. .......... 424/422 |
| 7,413,747 B2 | 8/2008 | Mueller et al. ........... 424/448 |
| 7,632,859 B2 | 12/2009 | Li et al. ................ 514/438 |
| 2003/0026830 A1* | 2/2003 | Lauterback et al. ....... 424/449 |
| 2003/0027793 A1 | 2/2003 | Lautertback et al. ...... 514/63 |
| 2003/0166709 A1* | 9/2003 | Rimpler et al. .......... 514/447 |
| 2004/0034083 A1 | 2/2004 | Stephenson et al. ....... 514/406 |
| 2004/0048779 A1 | 3/2004 | Schollmayer ............. 514/2 |
| 2004/0081683 A1 | 4/2004 | Schacht et al. .......... 424/449 |
| 2004/0116537 A1 | 6/2004 | Li et al. ................ 514/663 |
| 2004/0137045 A1 | 7/2004 | Breitenbach et al. ...... 424/449 |
| 2004/0198753 A1 | 10/2004 | Kase et al. ............. 514/263.2 |
| 2004/0209861 A1 | 10/2004 | Benavides et al. ........ 514/210.01 |
| 2005/0032843 A1 | 2/2005 | Pieper et al. ........... 514/338 |
| 2005/0033065 A1 | 2/2005 | Mueller et al. .......... 549/74 |
| 2005/0079206 A1 | 4/2005 | Schacht et al. .......... 424/449 |
| 2005/0175678 A1 | 8/2005 | Breitenbach ............. 424/448 |
| 2005/0182090 A1 | 8/2005 | Mierau et al. ........... 514/304 |
| 2005/0197385 A1 | 9/2005 | Scheller et al. ......... 514/438 |
| 2005/0260254 A1 | 11/2005 | Breitenbach et al. ...... 424/449 |
| 2006/0263419 A1 | 11/2006 | Wolff ................... 424/448 |
| 2007/0072917 A1 | 3/2007 | Scheller et al. ......... 514/357 |
| 2007/0093546 A1 | 4/2007 | Scheller et al. ......... 514/447 |
| 2007/0191308 A1 | 8/2007 | Kramer ................... 514/60 |

(Continued)

FOREIGN PATENT DOCUMENTS

CA    2 532 804    2/2005

(Continued)

OTHER PUBLICATIONS

Dawson (2002) Nature Neuroscience Supplement, vol. 5, 1058-1061.

(Continued)

*Primary Examiner*—Sreeni Padmanabhan
*Assistant Examiner*—Sahar Javanmard
(74) *Attorney, Agent, or Firm*—Harness, Dickey & Pierce, P.L.C.

(57) ABSTRACT

The invention relates to the use of rotigotine, its salts and prodrugs, as a medicament for preventing and/or treating Parkinson's plus syndrome.

31 Claims, 2 Drawing Sheets

U.S. PATENT DOCUMENTS

| | | | |
|---|---|---|---|
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |

FOREIGN PATENT DOCUMENTS

| | | |
|---|---|---|
| CA | 2 532 859 | 2/2005 |
| CA | 2 547 820 | 6/2005 |
| CA | 2 546 797 | 7/2005 |
| CA | 2 568 850 | 2/2006 |
| EP | 1256339 | 11/2002 |
| WO | WO 93/00313 | 1/1993 |
| WO | WO 94/26703 | 11/1994 |
| WO | WO 96/31210 | 10/1996 |
| WO | WO 97/29735 | 8/1997 |
| WO | WO 99/49852 | 10/1999 |
| WO | WO 00/03715 | 1/2000 |
| WO | WO 00/02053 | 6/2000 |
| WO | WO 00/35954 | 6/2000 |
| WO | WO 00/38669 | 7/2000 |
| WO | WO 01/38321 | 5/2001 |
| WO | WO 01/39756 | 6/2001 |
| WO | WO 01/62249 | 8/2001 |
| WO | WO 02/15903 | 2/2002 |
| WO | WO 02/31499 | 4/2002 |
| WO | WO 02/38646 | 5/2002 |
| WO | WO 02/018382 | 7/2002 |
| WO | WO 02/089777 | 11/2002 |
| WO | WO 02/089778 | 11/2002 |
| WO | WO 03/007803 | 1/2003 |
| WO | WO 03/012137 | 2/2003 |
| WO | WO 03/029233 | 4/2003 |
| WO | WO 03/069332 | 8/2003 |
| WO | WO 03/076658 | 9/2003 |
| WO | WO 03/088958 | 10/2003 |
| WO | WO 2004/012719 | 2/2004 |
| WO | WO 2004/012721 | 2/2004 |
| WO | WO 2004/012730 | 2/2004 |
| WO | WO 2004/050083 | 6/2004 |
| WO | WO 2004/058247 | 7/2004 |
| WO | WO 2005/070428 | 8/2005 |
| WO | WO 2006/050976 | 3/2006 |
| WO | WO 2006/039532 | 4/2006 |

OTHER PUBLICATIONS

Den Daas (1990) Naunyn-Schmiedeberg's Archives of Pharmacology 341, 186-191.
Den Daas (1990) Naunyn-Schmiedeberg's 342, 655-659.
Den Daas (1991) J. Pharm. Pharmacology 43, 11-16.
Eberhardt (2003) Toxicology Letter 139(2), 135-151.
Fahn et al. (1987) Recent Developments in Parkinson's Disease vol. 2, pp. 153-163, 293-294.
Gerlach (2003) Neurotox. Res. 5(1), 43-51.
Hirsch (2003) Ann NY Academy Science 991, 214-228.
Hobson (2003) Can. J. Neurol. Sci. 30(Suppl 1) S2-S9.
Lev (2003) Prog. Neuropsychopharm. Biol. Psychiatry 27(2), 245.
Mark (2001) Neurol. Clin. 19(3), 607-627.
Metman (2001) Clinical Neuropharmcology 24(3), 163-169.
Michel et al. (2002) Rev. Neurol. (Paris) 158 Spec No. 1, pp. 7S24-7S32.
Mucke (2003) IDrugs 6(9), 894-899.
Neophytides et al. (1982) J. Neurology Neurosurgery Psychiatry 45, 261-263.
Newman-Tancredit et al. (2002) J. Pharm. And Experimental Ther. 303(2), 805-814.
Parkinson Study Group (2003) Arch. Neurol. 60(12), 1721-1728.
Pascual (1992) Annals of Neurology 32(5), 703-707.
Pierot (1988) J. Neurological Sciences 86, 291-306.
Tuite (2003) Expert Opin. Investig. Drugs 12(8), 1335-1352.
Vila (2003) Nat. Rev. Neurosci 4(5), 365.
Wenning et al. (2004) Lancet Neurology 3, 93-103.
Becker, et al. ( (2002) "Early diagnosis of Parkinson's disease." J Neurol 249(Suppl 3):III/40-III/48.
Gerlach, et al. (2003) "Neuromelanin and its interaction with iron as a potential risk factor for dopaminergic neurodegeneration underlying Parkinson's disease." Neurotoxicity Research 5(1):43-51.
Guttman, et al. (2003) Current concepts in the diagnosis and management on Parkinson's disease. CMAJ, 168(3):293-301.
Hughes, et al. (1992) "Accuracy of clinical diagnosis of idiopathic Parkinson's disease: a clinico-pathological study of 100 cases." Journal of Neurology, Neurosurgery, and Psychiatry 55:181-184.
Kihara, et al. (2002) "Protective effect of dopamine D2 agonists in cortical neurons via the phosphatidylinositol 3 kinase casade." J. Neurosci. Res. 70:274-282.
Martinez-Martin, et al. (1994) "Unified Parkinson's disease rating scale characteristics and structure." Movement Disorders 9(1):76-83.
McKay, et al. (2008) "Will stem cell biology generate new therapies for Parkinson's disease?" Neuron 58:659-661.
Nair, et al. (2003) "Activation of phosphoinositide 3-kinase by $D_2$ receptor prevents apoptosis in dopaminergic cell lines." Biochem. J. 373:25-32.
Oertel, et al. (2003) "New aspects in the treatment of Parkinson's disease." Akt Neurol 30(Suppl 2):S263-265.
Oertel, et al. (2003) "New aspects in the treatment of Parkinson's disease." Akt Neurol 30(Suppl 2):S263-265 (English Translation).
R & D Focus Drugs News, Aug. 20, 2001, "Drug delivery system, transdermal rotigotine Schwartz clinical data (treatment of Parkinson's disease." IMS World Pulications Ltd. ISSN:1350-1135.
Schapira (2002) "Neuroprotection and dopamine agonists." Neurology 58(Suppl 1):S9-S18.
Scheller, et al. (2007) "Rotigotine treatment partially protects from MPTP toxicity in a progressive macaque model of Parkinson's disease." Experimental Neurology 203:415-422.
Scheller, et al. (2008) "Neuroprotective effects of rotigotine in the acute MPTP-lesioned mouse model of Parkinson's disease." Neuroscience Letters 432:30-34.
Sherman (2001) "Augmentation strategy aids treatment-resistant depression. (Dopamine Agonist).(pramipexole for mental depression)." Clinical Psychiatry News p. 1-2.
Shoulson, et al. (2003) "A controlled trial of rotigotine monotherapy in early Parkinson's disease." Arch. Neurol. 60:1721-1728.
Takashima, et al. (1999) "Bromocriptine protects dopaminergic neurons from levodopa-induced toxicity by stimulating $D_2$receptors." Exp. Neurol. 159:98-104.
Thomas, et al. (2007) "Dopa-responsive pseudo-orthostatic tremor in Parkinsonism." Movement Disorders 22(11):1652-1656.
Tuite, et al. (2003) "Recent developments in the pharmacological treatment of Parkinson's disease." Expert Opin. Investig. Drugs 12(8):1335-1352.
Van der Weide, et al. (1988) "The enantiomers of the D-2 dopamine receptor agonist N-0437 discriminate between pre- and postsynaptic dopamine receptors." Eur J Pharmacol 146:319-326.
Abbas (1999) Hum. Mol. Genet 8, 567.
Balsara et al. (1982) Ind. J. Physiol. Pharmac. 26(3):1&3495.
Barzilai (2001) Cell Mol. Neurobiol. 21(3), 215-235.
Becker (2002) J. Neurol. 249(Suppl. 3) III/40-III/48.
Blanchet et al. (2004) Parkinsonism and Related Disorders 10, 297-304.
Borsini (1988) Eur. J. Pharmacol. 148, 301-307.
Burn (2000) The Pharmaceutical Journal 264, 476-479.
Camicioli (2002) R. Drugs Today (Barc) 38*10, 677-686.
Carp et al. (1982) Brain Research 242, 247-254.
Chan et al. (2004) Hospital Pharmacist 11, 18-22.
Chase et al. (1995) Clinical Neuropharmacology 18(1), S207-S215.
Collado-Seidet et al. (1999) CNS Drugs 12(1):9-20.
Domino et al. (1993) J. Pharmacol. & Experimental Therapy vol. 264(1), 221-225.
EMEA (2005) Scientific discussim (Siol), www.emea.wropa. eulhumandoCSmDFslEPAFVsif I/ 0591 97ei16.M~9 pp.
Foley et al. (2004) J. Neural Transmission 111, 1375-1446.
Gerlach et al. (2003) J. Neural Transm. 65(Suppl.), 167-183.

Guttman (2003) Canadian Med. Assoc. Journal 168(3), 293-301.
Hackling (2002) ChemBioChem 3, 947-961.
Hagan et al. (1997) Tips vol. 18, 156-163.
Hauser et al. (2004) Neurol. Clin. 22, S149-S166.
Henderson (2003) J. Neurol. Neurosurg. Psychiatry 74, 956.
Hoehn (1992) *Parkinson's Disease* 10(2):331-339.
Holcomb et al. (1982) Eur. J. Pharmacol. 82, 173-178.
Hornykiewicz (2002) Encyclopedia of Life Sciences vol. 13, 695-704.
Hughes (1992) J. Neurol. Neurosurg. Psychiatry 55, 181-184.
Hutchinson et al. (1999) J. Neurol. Neurosurg. Psychiatry 67, 815-818.
Jackson et al. (1989) NaunynSchmiedeberg's Arch. Pharmacol. 340:35S365.
Joyce (2001) Pharmacol. & Ther. 90, 231-259.
Kitada (1998) Nature 392, 605-608.
Korczyn et al. (2002) Drugs 62(5), 775-786.
Krygowska-Wajs (2000) Funct. Neurol. 15, 41.
Kulkarni & Verma (1992) Drugs of Today 28(3):201-217.
Lee et al. (1982) Psychiatry Research 7, 111-119.
Levien (2005) Advances in Pharmacy 3(1), 62-92.
Li et al. (2000) Proceed Intl. Symp. Control Rel. Bioact. Mater, pp. 952-953.
Li et al. (2001) Pharm. Research vol. 18(11), 1509-1513.
Linazasoro (2004) Movement Disorders 19(7), 743-754.
Lucking (2000) N. Engl. J. Med. 342, 1560-1567.
Mackonochie (2003) Mar. 31-Apr. 3 Stuttgart, GER, Drug Discovery Tech. 2003 Seventh Annual Conference and Exhibition, vol. 6, 420-422.
Matsumine (1997) Am. J. Hum. Genet. 60, 588.
Modigh et al. (1984) Neurotransmitter & Receptor Mechanisms, 18-27.
Mouradian & Chase (1989) Curr. Opin. Neurol. Neurosurg. 2:30+313.
Muramatsu et al. (2003) GLIA 42, 307-313.
Nair (2003) Movement Disorders 18(7); 738-750.
Nurse et al. (1984) Neurochemical Research 9(9), 1231-1238.
Nussbaum (2003) N. Engl. J. Medicine 348(14),1356-1364.
Pankratz (2003) Am. J. Hum. Genet. 72, 1053-1057.
Park (2002) Drug Delivery Technology 2(5), Jul.//Aug., http://www.drugdeliverytech.com/cgi-bin/issues.cgi?idIssue=6 and http://www.drugdeliverytech.com/cgi-bin/articles.cgi?idArticle=60.
Paulus & Trenkwalder (2006) Lancet Neurol. 5 (neurolosv.thelancet.com), 9 pp.
Polymeropoulos (1997) Science 276, 2045-2047.
Prunier (2003) NeuroImage 19, 810-816.
Rammsayer (1997) Int. J. Neurosci. 91, 45.
Rascol, et al. (2002) "Treatment interventions for Parkinson's disease: an evidence based assessment." Lancet 359:1589-1598.
Riederer (2000) J. Neurol. 247(4), IV/36-IV/37.
Scriabine (2003) CNS Drug Reviews 9(4), 389-395.
Sharma (2002) Neurol. Clin. N. Am. 20, 759-778.
Stern (2004) Annals of Neurology 56(2), 169-170.
Stiasny-Kolster et al. (2000) Sleep, May 1, 23(3), 1-6.
Stichel and Scheller (2005) EFNS Conference, "Rotigotine Prevents Neurodegeneration in a Mouse Model of Parkinson's Disease".
Stockmeier et al. (1997) Neuropsychopharmacology 16(2), 162-173.
Strange (1993) Neurochem. Int. 22(3):223-236.
Swart (1993) Toxicology Methods 3, 279, 289 last paragraph.
Swart (1994) J. Analytical Toxicology 18, 71-77.
Swart (1995) Pharmaceutical Sciences 1, 437-440.
Tassin (1998) Am. J. Hum. Genet. 63, 88-94.
Timmerman (1993) Pharm. World Sci. 15(2):90-92.
Valente (2001) Am. J. Hum. Genet. 68, 895.
van der Geest et al. (1997) Pharm. Research vol. 14, 1798-1803.
Van Dujin (2001) Am. J. Hum. Genet. 69, 629-634.
Vanacore (2002) Neurol. Sci. 23, S119.
Waters (2005) Movement Disorder 20(1), S38-S44.
Wikstrom (1992) in Ellis & Luscombe, eds. "Progress in Medical Chemistry" vol. 29, pp. 199-216; Elsevier.
Office Action, dated Sep. 12, 2008 issued in U.S. Appl. No. 10/429,283.
Office Action, dated Mar. 30, 2009 issued in U.S. Appl. No. 10/429,283.
Office Action, dated Dec. 23, 2009 issued in U.S. Appl. No. 10/429,283.
Office Action, dated Feb. 19, 2009 issued in U.S. Appl. No. 10/585,609.
Office Action, dated Sep. 14, 2009 issued in U.S. Appl. No. 10/585,609.
Office Action, dated Dec. 10, 2008 issued in U.S. Appl. No. 11/060,997.
Office Action, dated Jun. 29, 2009 issued in U.S. Appl. No. 11/060,997.
Office Action, dated Mar. 29, 2010 issued in U.S. Appl. No. 11/060,997.

* cited by examiner

Figure 1:
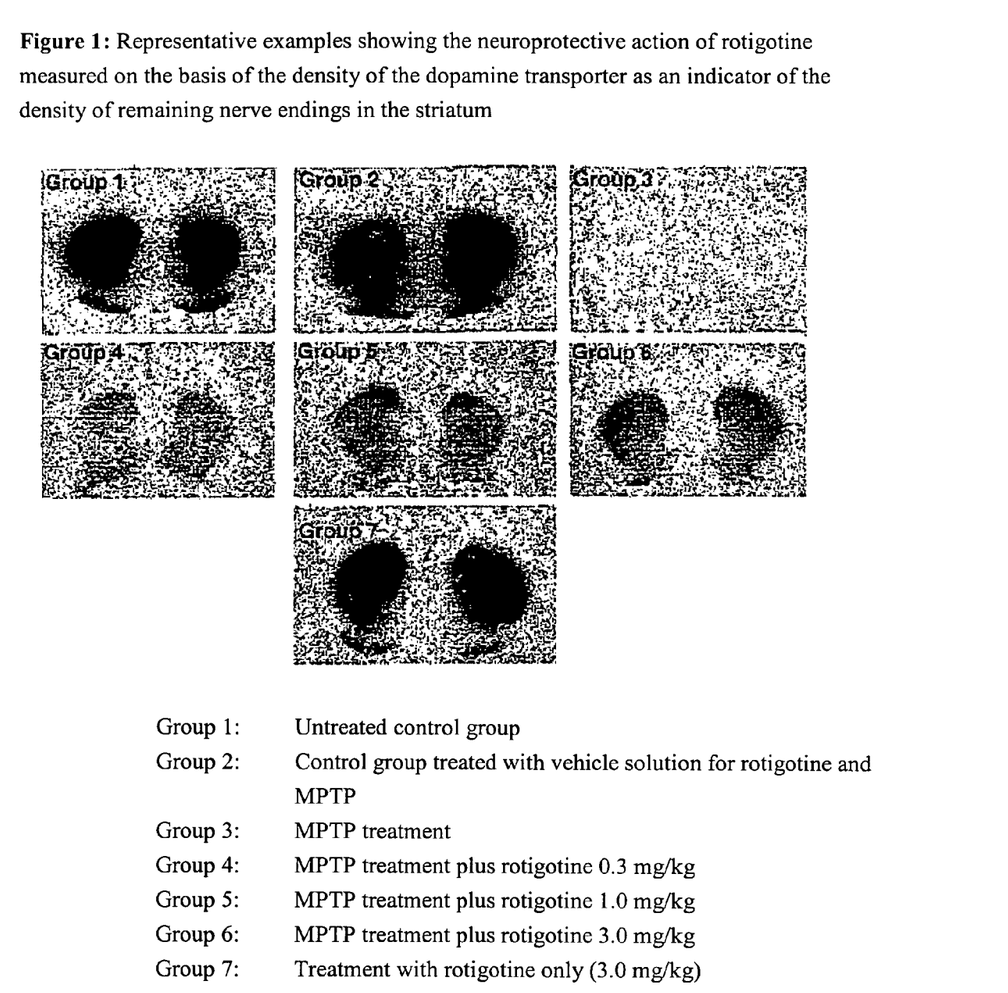

Figure 1: Representative examples showing the neuroprotective action of rotigotine measured on the basis of the density of the dopamine transporter as an indicator of the density of remaining nerve endings in the striatum

| | |
|---|---|
| Group 1: | Untreated control group |
| Group 2: | Control group treated with vehicle solution for rotigotine and MPTP |
| Group 3: | MPTP treatment |
| Group 4: | MPTP treatment plus rotigotine 0.3 mg/kg |
| Group 5: | MPTP treatment plus rotigotine 1.0 mg/kg |
| Group 6: | MPTP treatment plus rotigotine 3.0 mg/kg |
| Group 7: | Treatment with rotigotine only (3.0 mg/kg) |

Figure 2:
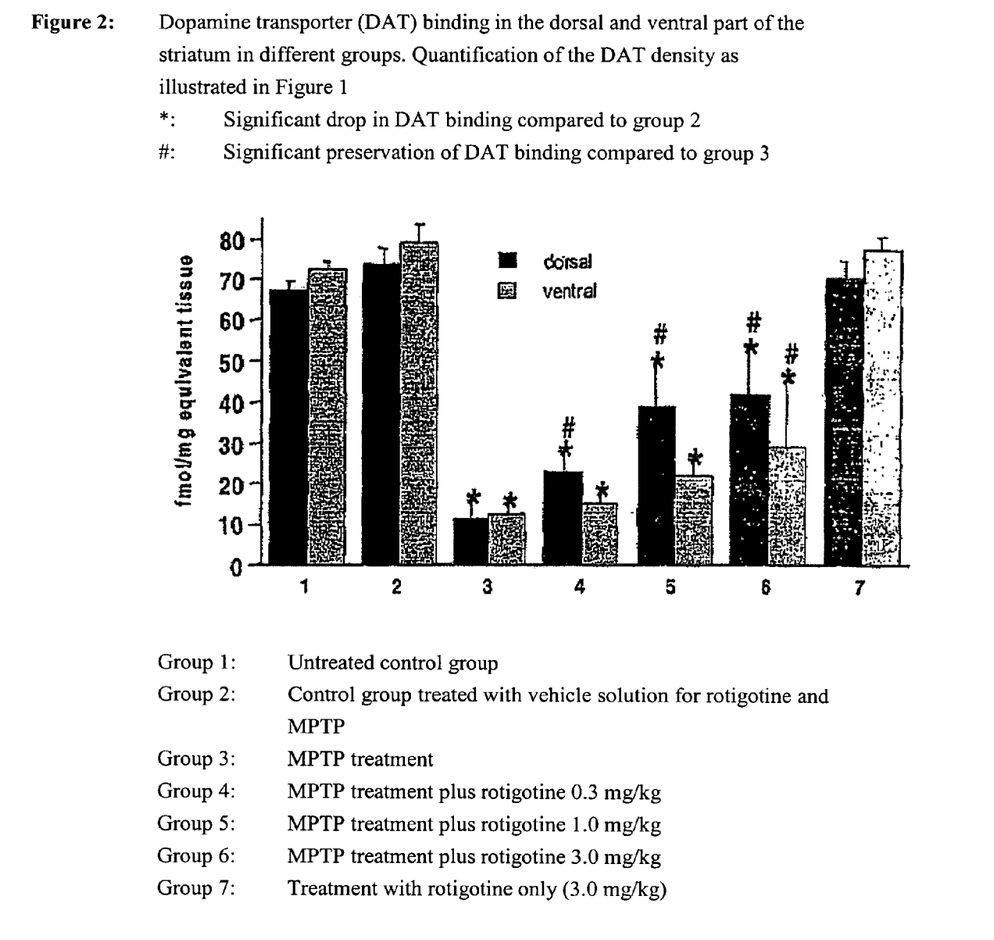

Figure 2: Dopamine transporter (DAT) binding in the dorsal and ventral part of the striatum in different groups. Quantification of the DAT density as illustrated in Figure 1

\*: Significant drop in DAT binding compared to group 2
\#: Significant preservation of DAT binding compared to group 3

Group 1: Untreated control group
Group 2: Control group treated with vehicle solution for rotigotine and MPTP
Group 3: MPTP treatment
Group 4: MPTP treatment plus rotigotine 0.3 mg/kg
Group 5: MPTP treatment plus rotigotine 1.0 mg/kg
Group 6: MPTP treatment plus rotigotine 3.0 mg/kg
Group 7: Treatment with rotigotine only (3.0 mg/kg)

USE OF ROTIGOTINE FOR TREATING AND PREVENTING PARKINSON'S PLUS SYNDROME

CROSS REFERENCE TO RELATED APPLICATIONS

This application is a U.S. national stage filing under 35 U.S.C. §371 of International Application No. PCT/EP2005/003013 filed on Mar. 22, 2005, which claims priority of German Application No. DE 10 2004 014 841 filed on Mar. 24, 2004. This application contains subject matter that may relate to presently filed and co-assigned U.S. Applications titled "Use of rotigotine for treatment or prevention of dopaminergic neuron loss" (Ser. No. 11/060,997) and "Use of Substituted 2-Aminotetralines for the Preventative Treatment of Parkinson's Disease" (Ser. No. 10/585,609).

FIELD OF THE INVENTION

The present invention relates to methods and medicinal preparations for the prevention and/or treatment of Parkinson's plus syndrome.

BACKGROUND OF THE INVENTION

The term "Parkinson's plus syndrome" covers several idiopathic diseases which are associated with the occurrence of symptoms which are Parkinson-like but that may be differentiated by diagnostic and clinical/pathophysiological means from Parkinson's disease.

The diseases classed as Parkinson plus syndrome (PPS) include multiple system atrophies (MSA), progressive supranuclear palsy (PSP), corticobasal ganglionic degeneration (CBGD) and dementia with Lewy bodies (DLB).

Multiple system atrophies subsume, in particular, Shy-Drager syndrome, olivopontocerebellar atrophy (OPCA) and striatonigral degeneration (SND). See Mark et al, *Neurol Clin*. 2001, 19(3): 607.

The assignment of Pick's disease, hemiparkinsonism and parkinsonism in Alzheimer's and ALS patients and the Westphal variant of Huntington's chorea to PPS is not uniform in specialist literature, but for the purposes of the present patent application, these diseases are considered to be subsumed under the term PPS in accordance with the classification used by Hobson et al, *Can J Neurol Sci*. 2003 March; 30 Suppl 1: p 2.

Common to the diseases subsumed under Parkinson's plus syndrome is the lack of, or rapidly diminishing, response to L-dopa or dopamine agonists and additional symptoms such as cerebellar or pyramidal signs, early or severe dementia plus speaking and swallowing disorders in the early phase (Mark 2001, supra; Gerlach et al, Die Parkinson-Krankheit, Springer, Vienna N.Y., 2003).

For an overview of differential-diagnostic criteria and classification of some symptoms for several Parkinson's plus syndromes and Parkinson's disease (also known as idiopathic Parkinson's syndrome, IPS), Table 1 is provided below.

TABLE 1

| | Parkinson's plus syndrome | | | | |
| --- | --- | --- | --- | --- | --- |
| | Multiple system atrophy | | | | |
| | SND | OPCA | CBD | PSP | IPS |
| Rigor/akinesia | ++ | + | ++/+++ | ++/+++ | ++/+++ |
| Cerebellar signs | + | ++ | − | − | − |
| Pyramidal signs | − | ++ | ++ | + | − |
| Postural instability | + | + | + | +++ | + |
| Dementia | − | − | + | + | + |
| Oculomotor disorders | + | (+) | + | +++ | + |
| Dysphagia | − | + | ++ | ++ | + |
| Retrocollis | − | − | − | ++ | − |
| Sphincter disorders | + | + | − | − | − |
| Impotence | + | + | ++ | + | + |

SND: striatonigral degeneration
OPCA: olivopontocerebellar atrophy
CBD: corticobasal degeneration
PSP: progressive supranuclear palsy
IPS: idiopathic Parkinson's syndrome Table 1 is based on Mark MH, Lumping and splitting the Parkinson plus syndromes: dementia with Lewy bodies, multiple system atrophy, progressive supranuclear palsy, and corticalbasal ganglionic degeneration. Neurol Clin. 2001 August; 19(3): 607-27. The table is also modified according to Gerlach M, Reichmann H, Riederer P, Die Parkinson-Krankheit, Springer Vienna N.Y., 2003.

Computed tomography is an important criterion when differentiating between IPS and PPS. Patients with IPS display normal dopamine receptor levels in the SPECT until the late stages, while PPS patients demonstrate an early loss of pre- and postsynaptic dopaminergic neurons, which is associated with an identifiable reduction in the density of dopamine receptors. PET analyses confirm a reduced L-dopa content and L-dopa metabolism in IPS patients (Gerlach et al., 2003, supra).

Due to the frequently absent or poor response to L-dopa, drug treatment for PPS is difficult and generally consists in a symptomatic therapy for specific individual symptoms, e.g. treatment for hypotension.

Dopamine receptor agonists are generally ineffective for the treatment of PPS (Mark, 2001, supra). In exceptional cases, there have been reports of a certain therapeutic success with individual dopamine agonists, although these effects appear to be substance-specific. For example, Wenning et al (Lancet, 2004, 3, 93) reported on the therapeutic success of bromocriptine in a trial with six patients, while a controlled trial with lisuride found no efficacy. Since it is known that the majority of dopamine agonists do not act on one sole dopamine receptor, but have a complex receptor profile (Newman-Tancredi, J Pharmacol Exp Ther 2002, 303, 805), the reason for the efficacy of bromocriptine could be the special features of the receptor profile or other not further characterised substance-specific properties.

Parkinson's plus syndrome is generally linked to a dopaminergic neurodegeneration in the substantia nigra (Mark, 2001, supra). Therefore, successful therapy could be expected from the use of effective neuroprotectives which inhibit the progressive degradation of dopaminergic neurons (Dawson and Dawson V L, Nat Neurosci. 2002 November; 5 Suppl: 1058).

Rotigotine [(−)5,6,7,8-tetrahydro-6-[propyl[2-(2-thienyl) ethyl] amino]-1-naphthol] is known from the prior art as a dopamine agonist and symptomatic therapy for Parkinson's disease.

WO 02/089777 describes, for example, the transdermal administration of rotigotine in Parkinson patients and the associated improvement in the UPDRS (Unified Parkinson's Disease Rating Scale) scores and this has also been described by other authors (Metman et al, Clin Neuropharmacol. 2001, 24(3):163; Mucke H A, Rotigotine Schwarz Pharma. IDrugs. 2003 September; 6(9):894; The Parkinson Study Group, Arch Neurol. 2003 60(12):1721).

The UPDRS score is an important tool for the diagnosis or treatment of patients with Parkinson's disease (Fahn S, Elton R L, Members of the UPDRS Development Committee (1987) Unified Parkinson's Disease Rating Scale. In: Fahn, S, C D Marsden, D B Calne, M Goldstein (eds) Recent Developments in Parkinson's Disease. Vol II. Macmillan Healthcare Information, Florham Park (N.J.), pp 153-163, 293-304). However, the UPDRS score only determines the effect of an active substance on the symptoms of Parkinson's disease. It does not provide any information as to whether an active substance influences the dopaminergic cell destruction at the root of the symptoms.

However, apoptotic processes play an important role in the pathogenesis of Parkinson's plus syndrome in particular with regard to the destruction of dopaminergic neurons. See, for example, Lev et al, Prog Neuropsychopharmacol Biol Psychiatry. 2003; 27(2): 245; Michel et al, Rev Neurol (Paris). 2002; 158 Spec no 1: p 24. In addition, as reported in Hirsch et al (Ann N.Y. Acad Sci. 2003; 991: 214), various other neurodegenerative processes are thought to have a decisive influence on the development of parkinsonism and Parkinson's plus syndrome.

Therefore, there is a desire for neuroprotective substances that are able to stop or even reverse dopaminergic cell destruction (Vila et al, Nat Rev Neurosci. 2003; 4(5): 365). Here, the MPTP model is considered to be predictive for the required neuroprotective properties (Dawson, 2002, supra; Eberhardt O, Schulz J B, Toxicol Lett. 2003, 139(2-3): 135).

SUMMARY OF THE INVENTION

There is now provided a method for prevention and/or treatment of a Parkinson's plus syndrome in a patient, the method comprising administering to the patient a compound selected from the group consisting of rotigotine or physiologically acceptable salts or prodrugs thereof The Parkinson's plus syndrome prevented or treated herein can be, for example, multiple system atrophies, progressive supranuclear palsy, corticobasal degeneration, diffuse dementia with Lewy bodies or combinations thereof Common to these diseases subsumed under Parkinson's plus syndrome is a lack of or rapidly diminishing response to L-dopa or other dopamine agonists.

A therapeutic combination is further provided. The combination comprises rotigotine or a physiologically acceptable salt or prodrug thereof and at least one further active substance that prevents or reduces the rate of progression of dopaminergic cell loss in a patient.

In particular embodiments, the compound of the invention may be in a pharmaceutical form wherein the preparation can be administered orally, parenterally, transdermally or transmucosally. When a combination preparation is used, the pharmaceutical form can provide different release profiles for rotigotine and any further active substances.

A kit for treatment and/or prevention of Parkinson's plus syndrome is also provided. The kit includes a first medicinal preparation comprising rotigotine or a physiologically acceptable salt or prodrug thereof and a second medicinal preparation comprising at least one further active substance. The rotigotine and active substances may be administered to a subject simultaneously or in a temporally graduated manner.

DETAILED DESCRIPTION OF THE INVENTION

As may be seen in Table 2, and FIGS. 1 and 2, experimental investigations have now surprisingly revealed that rotigotine, which up to now has only been used for symptomatic therapy of idiopathic Parkinson's disease, has neuroprotective properties in mammals. Rotigotine surprisingly demonstrates the desired pharmacological profile in both an acute and a sub-acute MPTP model. The results of the investigation suggest that rotigotine prevents apoptotic processes.

For example, rotigotine demonstrates a neuroprotective action in a Parkinson's mouse model: following the acute administration of MPTP, which causes Parkinson's symptoms in humans and monkeys, on the one hand, the number of degenerating neurons in the acute phase was measured and on the other the functional integrity of the striatum in the sub-acute phase was established by determining the density of the dopamine transporter in the terminal nerve endings. It was possible to demonstrate in both cases that rotigotine had a neuroprotective action: on the one hand, the number of degenerating neurons in the mesencephalon was reduced following the administration of rotigotine (Table 2) and on the other the dopaminergic innervation of the striatum is virtually completely retained or restored (FIGS. 1 and 2).

The results set forth below in Table 2 indicate the number of acutely degenerating neurons in the MPTP mouse model shown with FluoroJade staining with and without treatment with a single administration of rotigotine:

TABLE 2

| Group | Number of degenerating neurons | Standard deviation |
| --- | --- | --- |
| 1: Vehicle-treated control | 2.0 | 2.4 |
| 2: MPTP intoxication | 73.5 | 34.0 |
| 3: MPTP intoxication + rotigotine 0.3 mg/kg | 66.7 | 30.5 |
| 4: MPTP intoxication + rotigotine 1.0 mg/kg | 76.8 | 41.6 |
| 5: MPTP intoxication + rotigotine 3.0 mg/kg | 34.9 | 31.9 |
| 6: MPTP-vehicle + rotigotine 3.0 mg/kg | 3.8 | 4.3 |

The neuroprotective action of rotigotine was also investigated on monkeys in a pilot study.

In the MPTP model used, which reflects the progressive course of dopaminergic cell destruction in primates, monkeys (macaques) were injected with subthreshold toxic doses of MPTP over several days. The parkinsonian symptoms developed in the model over a period of approximately 2 weeks. As soon as a specific degree of damage was reached, daily injections of rotigotine were provided in a formulation giving rise to a continuous plasma level over a 24 hour period. The injections of MPTP were stopped as soon as the motor activity in the controls had reduced by a specific degree (approximately 5 days later). The animals' behavior was evaluated every day. Six weeks after the commencement of the MPTP application, the injections of rotigotine were stopped and the animals were observed for a further two weeks with no treatment. It was noted that the motor activity of the animals significantly improved under treatment and also in the following wash-out phase.

At the end of rotigotine application or at the end of the wash-out phase, in each case one group of animals was sacrificed and the condition of the basal ganglia investigated histologically and biochemically. The density of the nerve endings in the striatum of the treated animals was much higher than it was in the untreated animals. The content of preproenkephalin, an indicator of the intact crosslinking in the 'indirect pathway' of the basal ganglia, indicated a tendency toward normalization after the treatment and after the wash-out phase.

The results show that the neuroprotective potential of rotigotine can also be demonstrated in a primate model of the dopaminergic cell destruction. Therefore, it can be assumed that there is an antiapoptotic, neuroprotective action in humans as well.

Therefore, rotigotine provides an active substance which is ideally suited for the production of a medicinal preparation for the treatment and/or prevention of dopaminergic neuron loss in patients with Parkinson's plus syndrome, since in addition to its neuroprotective action, the dopaminergic action of rotigotine can also be beneficial.

Compared to the previous use of rotigotine, which was restricted to the purely symptomatic dopaminergic treatment of Parkinson's disease-patients, the treatment of patients with Parkinson's plus syndrome is therefore disclosed as a new field of application and, to be precise, also for patients who do not respond, or respond inadequately, to treatment with L-dopa or dopamine agonists with no neuroprotective action.

Therefore, one subject matter of the invention is the use of rotigotine, its salts and prodrugs as medicaments for the prevention and/or treatment of Parkinson's plus syndrome, whereby the term Parkinson's plus syndrome includes the following diseases: multiple system atrophies, progressive supranuclear palsy, corticobasal degeneration, dementia with Lewy bodies, Pick's disease, hemiparkinsonism, parkinsonism in Alzheimer's and ALS patients and the Westphal variant of Huntington's chorea. The diseases to be treated with rotigotine are hereby preferably selected from the following group: multiple system atrophies, progressive supranuclear palsy, corticobasal degeneration and diffuse dementia with Lewy bodies.

Another subject matter of the invention is a method for treating a patient with Parkinson's plus syndrome by the administration of a therapeutically sufficient quantity of rotigotine, its salts and/or prodrugs or by the administration of a medicament containing rotigotine or one of its salts and/or prodrugs.

For the purposes of the present patent application, the "prodrugs" of rotigotine should be understood in particular to mean compounds which are cleaved, converted or metabolised in the human body, in particular in the plasma, or on passage through the skin or mucous membrane in a therapeutically effective quantity to form rotigotine.

Rotigotine has the following formula:

Therefore, the relevant prodrugs of rotigotine are in particular derivatives of the phenolic hydroxy group, in particular esters, e.g. aryl carbonyl esters, alkyl carbonyl esters or cycloalkyl carbonyl esters, in particular alkyl carbonyl esters and cycloalkyl carbonyl esters each with up to 6 carbon atoms, carbonates, carbamates, acetals, ketals, acyloxyalkyl ethers, phosphates, phosphonates, sulfates, sulfonates, thiocarbonyl esters, oxythiocarbonyl esters, thiocarbamates, ethers and silylethers.

The term "alkyl carbonyl esters" comprises compounds in which the oxygen atom of rotigotine is in each case bound to a —C(O)-alkyl group. An alkyl carbonyl ester is formally formed from the esterification of the phenolic hydroxy group with an alcanoic acid, e.g. with acetic acid, propionic acid, butyric acid, isobuyric acid or valeric acid.

The term "cycloalkyl carbonyl esters" comprises compounds in which in each case the oxygen atom of rotigotine is bonded to a —C(O)-cycloalkyl group.

The term "aryl carbonyl esters" comprises compounds in which in each case the oxygen atom of rotigotine is bonded to a —C(O)-aryl group.

The term "carbonates" comprises compounds in which in each case the oxygen atom of rotigotine is bonded to a —C(O)—O—R group.

The term "carbamates" comprises compounds, in which in each case the oxygen atom of rotigotine is bonded to a —C(O)—NRR1, —C(O)—NH—R1 or —C(O)—NH$_2$ group.

The term "acetals" comprises compounds, in which in each case the oxygen atom of rotigotine is bonded to a —CH(OR)R1 group The term "ketals" comprises compounds, in which in each case the oxygen atom of rotigotine is bonded to a —C(OR)R1R2 group The term "acyloxyalkyl ethers" comprises compounds, in which in each case the oxygen atom of rotigotine is bonded to a —CHR—O—C(O)—R1 or —CH$_2$—O—C(O)—R1 group.

The term "phosphates" comprises compounds, in which in each case the oxygen atom of rotigotine is bonded to a —P(O$_2$H)OR group.

The term "phosphonates" comprises compounds, in which in each case the oxygen atom of rotigotine is bonded to a —P(O$_2$H)R group.

The term "sulfates" comprises compounds, in which in each case the oxygen atom of rotigotine is bonded to a —S(O)$_2$OR group.

The term "sulfonates" comprises compounds, in which in each case the oxygen atom of rotigotine is bonded to a —S(O)$_2$R group.

The term "thiocarbonyl esters" comprises compounds, in which in each case the oxygen atom of rotigotine is bonded to a —C(═S)—R group.

The term "oxythiocarbonyl esters" comprises compounds, in which in each case the oxygen atom of rotigotine is bonded to a —C(=S)—O—R group.

The term "thiocarbamates" comprises compounds, in which in each case the oxygen atom of rotigotine is bonded to a —C(=S)—N—RR1, —C(=S)—NH—R1 or —C(=S)—NH$_2$ group.

The term "ethers" comprises compounds, in which in each case the oxygen atom of rotigotine is bonded to a —R group.

In the above definitions of prodrugs, each of R, R1, and R2 is independently selected from hydrogen, alkyl, cycloalkyl and aryl, and preferably from the group $C_{1-6}$ alkyl, $C_{3-10}$ cycloalkyl and phenyl.

"Alkyl" can be a branched or unbranched alkyl group which preferably has 1 to 10 C atoms, particularly preferably 1 to 6 C atoms. Alkyl groups can also be substituted with one or more substituents, for example with halogen.

"Cycloalkyl" is an alkyl group, which may consist of pure ring-forming C atoms or may optionally bear further branching C atoms. Preferred chain lengths are 3-10, particularly preferably 4-8 or 4-6 C atoms.

"Aryl" is preferably phenyl. Phenyl can optionally be substituted in one or more positions, e.g. with alkoxy, alkyl, halogen or nitro.

The production by reaction of rotigotine with corresponding reactive precursors, such as acid chlorides, acid anhydrides, carbamyl chlorides, sulfonyl chlorides etc., is known to a person skilled in the field of clinical chemistry and may be found in the relevant specialist literature. Examples in literature include: Bundgaard: Design of Prodrugs, Elsevier, Amsterdam, 1985; Higuchi and Stella: Pro-drugs as novel drug delivery systems in American Chemical Society, Washington DC, 1975; Sloan: Prodrugs—Topical and Ocular Drug Delivery, Ed: M. Dekker, 1992; Roche: Design of biopharmaceutical properties through prodrugs and analogs, Washington, DC, 1977.

Various prodrugs of the racemate of rotigotine (N-0437) and corresponding manufacturing instructions and investigational methods are described, for example, in Den Haas et al, Naunyn-Schmiedeberg's Arch Pharmacol 1990, 342, 655; Den Haas et al, Naunyn-Schmiedeberg's Arch Pharmacol 1990, 341, 186 and Den Haas et al, J Pharm Pharmacol 1991, 43. 11.

The basic suitability of a rotigotine derivative as a prodrug can be determined by incubating the compound under defined conditions with an enzyme cocktail, a cell homogenate or an enzyme-containing cell fraction and demonstrating that rotigotine can be formed in a sufficient quantity. A suitable enzyme mixture is, for example, contained in the S 9 liver preparation made by the company Firma Gentest, Woburn, Mass., USA. The use of at least one suitable enzyme mixture is described herein in the 5$^{th}$ embodiment of the Examples. Alternatively, incubation with fresh blood or plasma or even a homogenate of the hypodermis may be performed in order to demonstrate the liver-independent metabolization of the prodrug to form the active component. Transdermal application requires an in vitro examination of permeation on excised skin.

The final evidence of suitability and potential efficacy in the medical models is performed by determining the rotigotine formed from the prodrug in the plasma. In vivo, a prodrug should release sufficient rotigotine to achieve a therapeutically effective steady-state concentration of rotigotine in the plasma, as is already known from clinical or preclinical investigations. In this regard, effective concentrations are generally rotigotine concentrations of between 0.01 and 50 ng/mL, preferably between 0.05 ng and 20 ng/mL and particularly preferably between 0.1 and 10 ng/mL plasma.

Rotigotine is the (S)-enantiomer of 5,6,7,8-tetrahydro-6-[propyl[2-(2-thienyl)ethyl]amino]-1-naphtol. This means that the content of (R)-enantiomers in the medicament is low according to the invention. The (R)-enantiomer is preferably present with a content of <10 mole %, particularly preferably with a content of <2 mole % and quite particularly preferably with a molar content of <1%, based on the total quantity of rotigotine, in the medicament.

Rotigotine and its prodrug can be present as free bases or in the form of physiologically acceptable salts, e.g. in the form of hydrochloride, in the medicament.

"Physiologically acceptable salts" include non-toxic addition salts of rotigotine with organic or inorganic acids, e.g. rotigotine HCl.

There are various methods of application available for the administration of rotigotine and its prodrugs which a person skilled in the art can select and adjust according to the requirement, condition and age of the patient, the required dose and desired application interval.

A preferred method for the administration of rotigotine is transdermal administration. The pharmaceutical form can in principle be selected from, for example, ointment, paste, spray, film, plaster or an iontophoretic device.

Preferably, rotigotine is in this regard applied to the patient's skin in plaster form, whereby the active substance is preferably present in a matrix of adhesive polymer, e.g. a self-adhesive polysiloxane. Examples of suitable transdermal formulations may be found in WO 99/49852, WO 02/89777, WO 02/89778, WO 04/58247, WO 04/12730, WO 04/12721 or WO 04/50083. A pharmaceutical form of this kind permits the establishment of an extensively constant plasma level and hence constant dopaminergic stimulation over the entire application interval. See, for example, WO 02/89778; or Metman, Clinical Neuropharmacol 24, 2001, 163.

If, on the other hand, a medicinal product in the form of a subcutaneous or intramuscular depot form is desired, the rotigotine can, for example, be suspended as a salt crystal, e.g. as a crystalline hydrochloride, in a hydrophobic, anhydrous medium and injected, as described in WO 02/15903. Rotigotine can also administered in the form of microcapsules, microparticles or implants based on biodegradable polymers, such as is described, for example, in WO 02/38646.

Other conceivable forms for the administration of rotigotine and its prodrug are transmucosal formulations, e.g. sublingual or nasal sprays, rectal formulations or aerosols for pulmonary administration.

Suitable doses of rotigotine are between 0.05 and approximately 50 mg/day, whereby preferably daily doses of between 0.1 and 40 mg and in particular between 0.2 and 20 mg/day are administered. In this regard, the dose can be increased gradually, which means that the treatment can optionally be commenced with low doses which are then increased to the maintenance dose.

It is evident to a person skilled in the art that the dosage interval may be varied according to the quantity applied, the method of application and the patient's daily requirement. For example, a formulation for transdermal application is conceivable, for example for once-a-day, three-day or seven-day administration while a subcutaneous or intramuscular depot can permit injections in a one, two or four-weekly cycle, for example.

In the neuroprotective pharmaceutical form, in addition to rotigotine, other active substances can be present which prevent the progression of dopaminergic cell loss.

Examples of this include substances with an antiapoptotic action (minocyclins, FK-506, cyclosporin A, zVAD) and neurotrophins, such as, for example, glial cell derived neurotrophic factor (GDNF).

In a combination preparation, the release of the active substances used in each case can take place to a large extent simultaneously or even sequentially. Sequential administration can, for example, be achieved by a pharmaceutical form, e.g. an oral tablet, having two different layers with different release profiles for the different pharmaceutically active components. A combination preparation according to the invention comprising a rotigotine formulation can alternatively also take the form of a "kit of parts" in which the antiapoptotic active substances to be administered are present in formulations which are separate from each other, which are then administered simultaneously or in a temporally graduated manner.

It is evident to a person skilled in the art that, in the context of the present invention, different pharmaceutical forms and application schedules are conceivable, all of which are objects of the invention.

EXAMPLES

Embodiments

1st Embodiment: Rotigotine Plasters 1.8 g rotigotine (free base) were dissolved in 2.4 g ethanol and added to 0.4 g Kollidon 90F (dissolved in 1 g ethanol). This mixture was added to a 74% solution of silicone polymers (8.9 g BioPSA 7-4201+8.9 g BIO-PSA 7-4301 [Dow Corning]) in heptane. After the addition of 2.65 g petroleum ether, the mixture was agitated for 1 hour at 700 rpm to obtain a homogeneous dispersion. After lamination on polyester, it was dried at 50° C. The final weight of the plaster was 50 g/cm$^2$.

2nd Embodiment: Rotigotine Depot Suspensions 1411.2 g Miglyol 812 were weighed in a Duran flask. 14.4 g Imwitor 312 were added to the Miglyol and then heated for 30 minutes under agitation to 80° C. The clear solution was cooled to room temperature and filtered.

(b) 1188 g of the solution produced in (a) were transferred to a glass laboratory reactor, 12 g rotigotine HCl added and homogenised for 10 minutes with an Ultraturrax at 10000 rpm under nitrogen. The suspension was filled into brown glass flasks with a running Ultraturrax (2000 rpm).

3rd Embodiment: Subacute MPTP Model

To induce intoxication, mice were administered 80 mg/kg of the neurotoxin 1-methyl-4-phenyl-1,2,3,6-tetrahydro-pyridine (MPTP) (in portions of 20 mg/kg in two-hourly intervals, groups 3-6 in FIGS. 1 and 2) resulting in the degeneration of about 50-60% of the neurons of the substantia nigra (maximum degeneration in group 3 in FIGS. 1 and 2). Rotigotine was administered daily in doses of 0.3, 1 or 3 mg/kg respectively over 7 days as a so-called 'slow-release formulation' (see embodiment 2) (groups 4-6 in FIGS. 1 and 2). A group of MPTP-treated animals (group 3) was given rotigotine-vehicle solution (see embodiment 2 without rotigotine HCl) and served as a reference. The controls were groups 1, 2 and 7, whereby group 1 is not given any treatment, group 2 is treated with the vehicle-solutions for MPTP and rotigotine, and group 7 was exclusively given rotigotine. The animals were sacrificed on day 8, their brains removed and frozen. Frozen sections were incubated with 100 pm[$^{125}$I] PE21 ([$^{125}$I]-(E)-N(3-iodoprop-2-enyl)-2β-carboxymethyl-3β-(4'-methylphenyl)-nortropane) in a phosphate buffer, pH 7.4 in order to mark the quantity of dopamine transporters still present in the striatum as an indicator of the quantity of functioning nerve endings. Rotigotine improves the survival of the neurons and the nerve endings in relation to the dose. This is clear evidence of the neuroprotective properties of the substance (FIG. 1 and 2).

4$^{th}$ Embodiment: Acute MPTP Model (Including Apoptose)

To induce intoxication, mice were administered 80 mg/kg of the neurotoxin 1-methyl-4-phenyl-1,2,3,6-tetrahydro-pyridine (MPTP) (in portions of 20 mg/kg at two-hourly intervals) resulting in the degeneration of approximately 50-60% of the neurons in the substantia nigra. Approximately 16 hours previously, rotigotine was added in doses of 0.3, 1 or 3 mg/kg respectively as a so-called 'slow-release formulation' (see embodiment 2). Diffusion and absorption latencies mean that rotigotine is optimally available when MPTP is added. Animals that were only given the vehicle solution (see embodiment 2 without rotigotine HCl) served as controls. After 24 hours, the animals were sacrificed and the brains fixed. The brain sections were stained with FluoroJade for the identification of degenerating cells. Immunohistochemical marking of the tyrosine hydroxylase was used to identify dopaminergic neurons. The staining of the tyrosine hydroxylase did not identify any differences between the treated and untreated animals; the FluoroJade staining revealed a large number of degenerating neurons; however, the neurons were not completely removed (which explains the absence of any difference between the tyrosine hydroxylase staining); this suggests that the cell destruction was taking place apoptotically and was not completed at the time of measurement (the apoptotic cells had not been completely dissolved or phagocyted). The number of the degenerating neurons was approximately 50% lower after the application of rotigotine, which is further confirmation of the neuroprotective properties of the substance (Table 2).

5$^{th}$ Embodiment: in vitro Conversion of a Prodrug into the Active Substance

The microsome fraction containing the essential metabolic enzymes was obtained from liver cell homogenates from humans, monkeys, dogs, rats and/or mice by differential centrifugation; alternatively, it is also possible to obtain the cytoplasmatic fraction. The subcellular fraction was suspended with a buffer in such a way that a solution with a defined protein content was obtained. After the addition of 1 μm of the prodrug to be tested, it was incubated at 37° C. for 60 minutes. Then rotigotine was quantified by means of HPLC/UV or by means of HPLC/MS and related to the quantity used. For more detailed analyses, concentration or time series were investigated.

The invention claimed is:
1. A method for treatment of a Parkinson's plus syndrome in a patient, comprising administering to the patient a compound selected from the group consisting of rotigotine, a physiologically acceptable salt of rotigotine, and a rotigotine prodrug, wherein the compound is administered to provide a rotigotine dosage of 0.05 mg to approximately 50 mg per day.
2. The method of claim 1 wherein the Parkinson's plus syndrome is selected from the group consisting of a multiple system atrophy, progressive supranuclear palsy, corticobasal degeneration, diffuse dementia with Lewy bodies, and a combination thereof.

3. The method of claim 1, wherein the patient fails to respond to L-dopa treatment.

4. The method of claim 1, wherein the compound is administered orally, parenterally, transdermally or transmucosally.

5. The method of claim 1, wherein the compound provides an extensively constant plasma level of rotigotine in the plasma of the patient over an application interval.

6. The method of claim 4, wherein the compound is administered transdermally.

7. The method of claim 1, wherein the compound is administered to provide a plasma level of rotigotine between 0.01 and 50 ng/mL.

8. The method of claim 7, wherein the rotigotine achieves a steady-state plasma level.

9. The method of claim 1, wherein the compound is administered to provide a plasma level of rotigotine between 0.05 and 20 ng/mL.

10. The method of claim 1, wherein the compound is administered to provide a plasma level of rotigotine between 0.1 and 10 ng/mL.

11. The method of claim 1, wherein rotigotine is administered in the form of a prodrug that is an ether, ester, thiocarbonyl ester, carbamate, thiocarbamate, carbonate, acetal, ketal, acyloxy alkyl ether, oxythiocarbonyl ester, phosphate, phosphonate, sulfate, sulfonate or silylether of rotigotine.

12. The method of claim 11, wherein the prodrug is a $C_{1-6}$ alkyl carbonyl ester of rotigotine.

13. The method of claim 1, wherein the compound is rotigotine hydrochloride.

14. The method of claim 1, further comprising administering at least one further active agent effective for treatment of the Parkinson's plus syndrome, wherein the at least one further active agent is selected from the group consisting of an antiapoptotic substance, a neurotrophin, and a combination thereof.

15. The method of claim 14, wherein the compound and the at least one further active substance are separate and are administered to the patient simultaneously.

16. The method of claim 14, wherein the compound and the at least one further active substance are separate and are administered to the patient in a temporally graduated manner.

17. A method for treatment of a Parkinson's plus syndrome in a patient, comprising administering to the patient a compound selected from the group consisting of rotigotine, a physiologically acceptable salt of rotigotine, and a rotigotine prodrug, wherein the compound is administered to provide a plasma level of rotigotine between 0.01 and 50 ng/mL.

18. The method of claim 17 wherein the Parkinson's plus syndrome is selected from the group consisting of a multiple system atrophy, progressive supranuclear palsy, corticobasal degeneration, diffuse dementia with Lewy bodies, and a combination thereof.

19. The method of claim 17, wherein the patient fails to respond to L-dopa treatment.

20. The method of claim 17, wherein the compound is administered orally, parenterally, transdermally or transmucosally.

21. The method of claim 17, wherein the compound provides an extensively constant plasma level of rotigotine in the plasma of the patient over an application interval.

22. The method of claim 20, wherein the compound is administered transdermally.

23. The method of claim 17, wherein the rotigotine achieves a steady-state plasma level.

24. The method of claim 17, wherein the compound is administered to provide a plasma level of rotigotine between 0.05 and 20 ng/mL.

25. The method of claim 17, wherein the compound is administered to provide a plasma level of rotigotine between 0.1 and 10 ng/mL.

26. The method of claim 17, wherein rotigotine is administered in the form of a prodrug that is an ether, ester, thiocarbonyl ester, carbamate, thiocarbamate, carbonate, acetal, ketal, acyloxy alkyl ether, oxythiocarbonyl ester, phosphate, phosphonate, sulfate, sulfonate or silylether of rotigotine.

27. The method of claim 24, wherein the prodrug is a $C_{1-6}$ alkyl carbonyl ester of rotigotine.

28. The method of claim 17, wherein the compound is rotigotine hydrochloride.

29. The method of claim 17, further comprising administering at least one further active agent effective for treatment of the Parkinson's plus syndrome, wherein the at least one further active agent is selected from the group consisting of an antiapoptotic substance, a neurotrophin, and a combination thereof.

30. The method of claim 27, wherein the compound and the at least one further active substance are separate and are administered to the patient simultaneously.

31. The method of claim 27, wherein the compound and the at least one further active substance are separate and are administered to the patient in a temporally graduated manner.

* * * * *

UNITED STATES PATENT AND TRADEMARK OFFICE
CERTIFICATE OF CORRECTION

| | | |
|---|---|---|
| PATENT NO. | : 7,872,041 B2 | Page 1 of 1 |
| APPLICATION NO. | : 10/593964 | |
| DATED | : January 18, 2011 | |
| INVENTOR(S) | : Dieter Scheller | |

It is certified that error appears in the above-identified patent and that said Letters Patent is hereby corrected as shown below:

Column 3, line 49, "thereof" should be changed to -- thereof. --.

Column 3, line 53, "thereof" should be changed to -- thereof. --.

Column 6, line 44, "group" should be changed to -- group. --.

Column 6, line 47, "group" should be changed to -- group. --.

Column 12, line 31, "claim 24" should be changed to -- claim 26 --.

Column 12, line 41, "claim 27" should be changed to -- claim 29 --.

Column 12, line 44, "claim 27" should be changed to -- claim 29 --.

Signed and Sealed this
Thirteenth Day of December, 2011

David J. Kappos
*Director of the United States Patent and Trademark Office*